(12) United States Patent
Clark et al.

(10) Patent No.: US 6,355,460 B1
(45) Date of Patent: Mar. 12, 2002

(54) METAL MEDIATED SERINE PROTEASE INHIBITORS

(75) Inventors: James M. Clark, San Mateo; Kyle Elrod, Fremont; Thomas E. Jenkins, LaHonda; Bradley A. Katz, San Francisco; William R. Moore, Burlingame; Robert M. Stroud, San Francisco, all of CA (US)

(73) Assignee: Axys Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 09/351,869

(22) Filed: Jul. 12, 1999

Related U.S. Application Data

(63) Continuation of application No. 08/746,986, filed on Nov. 19, 1996, now Pat. No. 6,255,091, which is a continuation-in-part of application No. 08/430,742, filed on Apr. 28, 1995, now Pat. No. 5,693,515.

(51) Int. Cl.$^7$ .............................. C12N 9/99; C12Q 1/37
(52) U.S. Cl. ............................ 435/184; 435/23; 435/24
(58) Field of Search ............................ 435/23, 24, 184

(56) References Cited

U.S. PATENT DOCUMENTS 5,145,841 A * 9/1992 Cullis-Hill et al.

OTHER PUBLICATIONS

Otani et al., "Studies on the Proteolytic Enzymes of Fungi, I.Effects of Metal Chelate Compounds on a Alkaline–Protease of *Aspergillus oryzae*" (1969a) J. Ferment. Technol., 47(1), pp. 20–24 (with translation).*

Otani et al., "Studies on the Proteolytic Enzymes of Fungi, II.Effects of Various Metal Chelates on a Alkaline Protease of *Aspergillus oryzae*" (1969b) J. Ferment. Technol. 47(7), pp. 424–429 (with translation).*

Ishikawa, "Inhibitory Conditions of the Tryptic Hydrolysis of p–Nitroanilide by Colloidal Dispersion Formed in the Reaction Mixture" (1971) Agr. Biol. Chem., 35(2) pp. 158–162.*

* cited by examiner

*Primary Examiner*—Jon P. Weber
(74) *Attorney, Agent, or Firm*—Townsend and Townsend and Crew LLP

(57) ABSTRACT

The present invention relates to serine protease inhibitors having a P site binding moiety and a divalent cation(s) chelating moiety which are pre-prepared as divalent cation (s) complexes or combined with the serine protease in the presence of divalent cation(s) and methods for identifying and using the inhibitors. The compounds are shown to have high inhibitory activity when complexed to divalent cation (s) and are useful in various processes associated with serine protease isolation and inhibition.

9 Claims, No Drawings

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 13 amino acids
      (B) TYPE: amino acid
      (C) STRANDEDNESS: <Unknown>
      (D) TOPOLOGY: linear (ii) MOLECULE TYPE: peptide (ix) FEATURE:
      (A) NAME/KEY: Peptide
      (B) LOCATION: 1..13
      (D) OTHER INFORMATION: /note= "serine protease substrate"

(ix) FEATURE:
      (A) NAME/KEY: Modified-site
      (B) LOCATION: 1
      (D) OTHER INFORMATION: /product= "OTHER"
          /note= "Xaa = 2,4-(dimethylamino)azobenzene-4'-sulfonyl
          arginine (dabsyl Arg)"

(ix) FEATURE:
      (A) NAME/KEY: Modified-site
      (B) LOCATION: 13
      (D) OTHER INFORMATION: /product= "OTHER"
          /note= "Xaa = 5-dimethylamino-1-naphthalenesulfonyl
          lysine (dansyl Lys)"

(xi) SEQUENCE DESCRIPTION: SEQ ID NO: 1:

```
Xaa Gly Val Val Asn Ala Ser Ser Arg Leu Ala Lys Xaa
1               5                   10
```

METAL MEDIATED SERINE PROTEASE INHIBITORS

CROSS-REFERENCES TO RELATED APPLICATIONS

This application is a continuation of application Ser. No.08/746,986, filed Nov. 19, 1996, now U.S. Pat. No. 6,255,091, which is a continuation-in-part of application Ser. No. 08/430,742, filed Apr. 28, 1995 (now U.S. Pat. No. 5,693,515).

FIELD OF THE INVENTION

This application relates to serine protease inhibitors, inhibitor-enzyme complexes formed by the serine protease inhibitors, methods of using the serine protease inhibitors and the inhibitor-enzyme complexes, and methods for determining whether compounds inhibit serine proteases.

DESCRIPTION OF THE FIELD

Serine proteases are produced within the cells of many living organisms and are often secreted to act outside of the producing cell. Individual serine proteases may target specific substrates (e.g., an inactive precursor for conversion to its biologically active form) or may act non-specifically (e.g., degradation of proteins or other peptides by scission). Further, individual serine proteases may be highly selective in that they recognize only one or a few related subsequences or non-selective in that they recognize and cleave a variety of unrelated sequences.

Serine proteases have a highly conserved active site, wherein specific amino acids which catalyze the bond scission have nearly identical spatial arrangements. A complementary binding site adjacent to the active site provides for the primary specificity of any individual serine protease. A succession of indentations or "pockets" along the surface of the protease serve to bind successive amino acid side chains along the substrate polypeptide chain on either side of the peptide bond to be cleaved. Substrate side chains which contribute to the association with the protease are designated P1, P2, P3, etc., proceeding from the side chain proximate to the susceptible bond toward the amino terminal of the protein, and P1', P2', P3', etc., proceeding from the side chain proximate to the susceptible bond toward the carboxyl terminal of the protein. Small molecules having suitable P binding moieties can be designed to mimic the substrate by occupying the substrate's binding site and inhibit the function of the serine protease.

Serine proteases provide a diverse array of biological functions. Important serine proteases include trypsin-like proteases, such as trypsin, tryptase, thrombin, plasma kallikrein, tissue kallikrein and factor Xa. Substrates for serine proteases are associated, for example, with blood clotting, complement mediated lysis, the immune response, glomerulonephritis, pain sensing, inflammation, pancreatitis, cancer, regulating fertilization, bacterial infection and viral maturation. Accordingly, appropriate drug therapies can comprise the inhibition of a particular serine protease implicated in the pathology and/or symptomatology of a disease. Hence, substantial interest exists in the identification of serine protease inhibitors which possess high selectivity for specific serine proteases.

The disclosure of other documents referred to throughout this application are incorporated herein by reference.

SUMMARY OF THE INVENTION

An aspect of this invention is a method for determining the serine protease inhibitory activity of a compound, which method comprises contacting the compound with a serine protease in a medium having present therein a divalent metal cation, wherein the cation has the capacity for interaction with the compound and thereby to potentiate any serine protease inhibitory activity possessed by the compound and the concentration of the divalent metal cation in the medium is modified to a level sufficient to produce any such interaction.

A second aspect of this invention is a method for determining whether the inhibitory activity of a serine protease inhibitor is potentiated by the presence of a divalent metal cation, which method comprises:

(a) assaying for the inhibition of a serine protease by the inhibitor, wherein the assay is conducted in a medium that is essentially devoid of dissociated divalent metal cations; and (b) assaying for the inhibition of the serine protease by the compound under essentially equivalent assay conditions to those used in Step (a), with the exception that the assay performed in Step (b) is conducted in a medium that contains an effective concentration of a divalent metal cation; wherein the inhibitory activity of the compound when measured by Step (b) is significantly greater than the inhibitory activity of the compound when measured by Step (a).

A third aspect of this invention is a method for inhibiting a serine protease with a serine protease inhibitor in a medium comprising the serine protease and the inhibitor, in which the inhibitor comprises two heteroatoms in spatial relationship one to the other so as to chelate a physiologically acceptable divalent metal cation capable of chelation, the improvement which comprises having sufficient quantity of the divalent metal cation in the medium or adding a sufficient amount of the divalent metal cation to the medium to have any or all of the inhibitor which is bound to the serine protease as a divalent metal cation complex, or providing the inhibitor as a divalent metal cation binary complex, such that the divalent metal cation is bound between the inhibitor and the serine protease as a divalent metal cation ternary complex.

A fourth aspect of this invention is a divalent metal cation binary complex of a compound of Formula I:

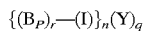

in which:

q is 0 and n is 1 or
q is 1 and n is 2;
Y is a bond or linking group of not more than six, typically not more than three and preferably carbon, atoms in a chain;
$B_P$ is a binding moiety for binding to one or more P sites of a serine protease;
r is 0 or 1, with the proviso that at least one $B_P$ binding moiety is present; and
I is a moiety that comprises at least one heteroatom when n is 2 and comprises at least two heteroatoms when n is 1, wherein two heteroatoms are in spatial relationship one to the other so as to be able to chelate the divalent metal cation in a bidentate manner.

A fifth aspect of this invention is a divalent metal cation ternary complex comprising the compound of Formula I in association with the divalent metal cation and a serine protease.

A sixth aspect of this invention is the serine protease inhibitors identified by the methods of this invention.

A seventh aspect of this invention is a method for treating a disease in an animal in which serine protease activity contributes to the pathology and/or symptomatology of the disease, which method comprises administering to the animal a therapeutically effective amount of a serine protease inhibitor identified by the methods of this invention.

Thus, it is intended that the scope of this invention encompasses any method for determining the serine protease inhibitory activity of a compound wherein the method requires the presence of a divalent metal cation and a serine protease and one of ordinary skill in the art could demonstrate that the cation has the capacity for interaction with a compound of Formula I and thereby to potentiate the inhibitory activity of the compound or is capable of chelating simultaneously with a compound of Formula I and the active site of the serine protease and thereby potentiate the inhibitory activity of the compound.

DETAILED DESCRIPTION OF THE INVENTION

Definitions

Unless otherwise stated, the following terms used in the specification and claims have the meanings given below:

"Alkyl" means a straight or branched, saturated or unsaturated hydrocarbon radical having the number of carbon atoms indicated (e.g., $(C_{1-8})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, etc.).

"Alkylene" means a straight, saturated or unsaturated hydrocarbon divalent radical (e.g., methylene, ethylene, vinylene, ethynylene, 2-propylene, 1-propylene, tetramethylene, isopropylidene, etc.).

"Amidino" means the radical —C(NH)NH$_2$.

"Amino" means the radical —NH$_2$.

"Aryl" means an aromatic monocyclic or polycyclic hydrocarbon radical containing the number of carbon atoms indicated, wherein the carbon atom with the free valence is a member of an aromatic ring (e.g., $(C_{6-14})$aryl includes phenyl, naphthyl, anthracenyl, phenanthrenyl, 1,2,3,4-tetrahydronaphth-5-yl, etc.).

"Arylene" means an aromatic monocyclic or polycyclic hydrocarbon divalent radical containing the number of carbon atoms indicated, wherein the carbon atoms with the free valence are members of an aromatic ring (e.g., $(C_{6-14})$arylene includes 1,2-phenylene, 1,3-phenylene, 1,2-naphthylene, 1,3-naphthylene, 1,3-anthracenylene, 1,3-anthracenylene, 1,2-phenanthrenylene, 1,2,3,4-tetrahydro-5,6-naphthylene, etc.)

"Cycloalkyl" means a saturated or unsaturated, monocyclic or polycyclic hydrocarbon radical containing the number of carbon atoms indicated, wherein the carbon atom with the free valence is a member of a non-aromatic ring (e.g., $(C_{3-14})$cycloalkyl includes cyclopropyl, cyclobutyl, cyclopentyl, cyclohexyl, cyclohexenyl, 2,5-cyclohexadienyl, bicyclo[2.2.2]octyl, 1,2,3,4-tetrahydronaphth-1-yl, etc.).

"Cycloalkylene" means a saturated or unsaturated, monocyclic or polycyclic hydrocarbon divalent radical containing the number of carbon atoms indicated, wherein the carbon atoms with the free valence are members of a non-aromatic ring (e.g., $(C_{3-6})$cycloalkylene includes 1,2-cyclopropylene, 1,2-cyclobutylene, 1,3-cyclobutylene, 1,2-cyclopentylene, 1,3-cyclopentylene, 1,2-cyclohexylene, 3-cyclohexen-1,2-ylene, 2,5-cyclohexadien-1,3-ylene, 1,2-bicyclo[2.2.2]octylene, 1,2,3,4-tetrahydro-1,2-naphthylene, etc.).

"Essentially devoid of dissociated divalent metal cations", as in a medium essentially devoid of dissociated divalent metal cations, means that the free concentration of the cation in the medium is so low as to have no or minimal capability of chelating with the prospective serine protease inhibitor.

"Effective concentration", as in a medium containing a compound, a serine protease and an effective concentration of divalent metal cation, means that the free concentration of cation in the medium is sufficient to produce an interaction with the compound, wherein the cation has the capacity for such interaction and thereby to potentiate any inhibitory activity of the compound, or to produce a simultaneous chelation with the compound and the active site of the serine protease, wherein the cation has the capacity for such chelation and thereby to potentiate the inhibitory activity of the compound.

"Free concentration", as in free concentration of divalent metal cation in a medium containing a compound and a serine protease, means that concentration of the cation of cation in the medium which is dissociated and free to interact with the compound, wherein the cation has the capacity for such interaction and thereby to potentiate any inhibitory activity of the compound, or to produce a simultaneous chelation with the compound and the active site of the serine protease, wherein the cation has the capacity for such chelation and thereby to potentiate the inhibitory activity of the compound.

"Guanidino" means the radical —NHC(NH)NH$_2$.

"Heteroalkylene" means alkylene, as defined above, wherein 1 to 5 of the carbon atoms indicated is replaced by a heteroatom chosen from N, O or S (e.g., amino, oxy, thio, azaethylene (—NHCH$_2$—), oxaethylene (—OCH$_2$—), etc.), with the proviso that the oxygen, nitrogen and sulfur atoms contained therein do not form bonds with other heteroatoms.

"Heteroaryl" means aryl, as defined above, wherein 1 to 5 of the carbon atoms indicated are replaced by a heteroatom chosen from N, O or S.

"Heteroarylene" means arylene, as defined above, wherein 1 to 5 of the carbon atoms indicated are replaced by a heteroatom chosen from N, O or S.

"Heteroatom" means nitrogen (N), oxygen (O) or sulfur (S).

"Heteroatom containing moiety", for the purposes of this application, means —OR, —NRR or —SR, wherein each R is independently alkyl, heteroalkyl, cycloalkyl, aryl, heterocycloalkyl, heteroaryl (e.g., methoxy, amino, methylamino, amidino, guanidino, anilino, hydroxy, mercapto, carboxy, methylacetoxy, glycinamido, cyclohexylamino, and the like.

"Heterocycloalkyl" for the purposes of this invention means an aromatic or non-aromatic, saturated or unsaturated, monocyclic or polycyclic, fused or non-fused, hydrocarbon radical containing at least one heteroatom and the number of carbon atoms indicated (e.g., pyrazole, imidazole, triazole, oxazole, thiazole, isoxazole, benzimidazole, pyran, pyridine, pyridazine, pyrimidine, pyrazine, dioxane, quinoline, isoquinoline, cinnoline, 2,2'-bis-imidazole, 2,2'-bis-pyridine, etc.).and comprised of four to seven, typically five to six, annular members and one to four, typically one to three and more preferably one to two, annular heteroatoms.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrobromic acid, hydrochloric acid, nitric acid, phosphoric acid, sulfuric acid and the like; or with organic acids such as acetic acid, benzenesulfonic acid, benzoic acid, camphorsulfonic acid, p-chlorobenzene-sulfonic acid, cinnamic acid, citric acid, cyclopentanepropionic acid, 1,2-ethanedisulfonic acid, ethanesulfonic acid, fumaric acid, glucoheptonic acid, gluconic acid, glutamic acid, glycolic acid, hexanoic acid, heptanoic acid, o-(4-hydroxybenzoyl) benzoic acid, 2-hydroxyethanesulfonic acid, hydroxynaphthoic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene- 1-carboxylic acid), muconic acid, 2-naphthalenesulfonic acid, oxalic acid, 3-phenylpropionic acid, propionic acid, pyruvic acid, salicylic acid, stearic acid, succinic acid, tartaric acid, tertiary butylacetic acid, p-toluenesulfonic acid, trimethylacetic acid and the like.

Pharmaceutically acceptable salts also include base addition salts which may be formed when acidic protons present are capable of reacting with inorganic or organic bases. Acceptable inorganic bases include aluminum hydroxide, calcium hydroxide, potassium hydroxide, sodium carbonate and sodium hydroxide. Acceptable organic bases include diethanolamine, ethanolamine, N-methylglucamine, triethanolamine, trometharnine and the like.

"Serine protease" means any enzyme that possesses a uniquely reactive serine residue that, through a mechanism of covalent attachment followed by hydrolysis, breaks amide bonds; thus, usually causing the degradation of proteins and peptides into smaller fragments. For the purposes of this invention, the definition of serine protease includes, but is not limited to protein C, chymase, chymotrypsin, cytomegalovirus protease, elastase, factor VIIa, factor IXa, factor Xa, plasm kallikrein, tissue kallikrein, β-lactamase, plasmin, thrombin, trypsin, tryptase and urokinase.

"Symptomatology" of a disease means any morbid phenomenon or departure from the normal in structure, function or sensation experienced by the patient and indicative of the disease, their production and the indications they finish.

"Therapeutically effective amount" means that amount which, when administered to an animal for treating a disease, is sufficient to effect such treatment for the disease.

"Treating" or "treatment" of a disease includes preventing the disease from occurring in an animal which may be predisposed to the disease but does not yet experience or display symptoms of the disease, inhibiting the disease (i.e., arresting its development) or relieving the disease (i.e., causing regression of the disease).

Presently Preferred Embodiments

While the broadest definition of this invention is set forth in the Summary of the Invention, certain aspects of the invention are preferred. For example, preferred is a method for determining the serine protease inhibitory activity of a compound, which method comprises contacting the compound with a serine protease in a medium having present therein a divalent metal cation selected from the group consisting of zinc and cobalt, wherein the cation has the capacity for interaction with the compound and thereby to potentiate any serine protease inhibitory activity possessed by the compound and the concentration of the divalent metal cation in the medium is modified to a level sufficient to produce any such interaction; more preferably wherein the divalent metal cation is zinc.

Preferred methods of this invention are those in which an amount of zinc is present in the assay medium that is at least equal to the concentration of the serine protease inhibitor. Generally, the amount of zinc included in a preparation or medium containing the inhibitor will be at least 0.1 $\mu$M, typically at least 1 $\mu$M, more preferably at least 1 $\mu$M, and more preferably at least 100 $\mu$M. Typically, the zinc concentration employed will provide that at least about 80%, preferably at least about 90%, and more preferably substantially all of the inhibitor will be chelated with zinc. In physiological systems, the amount of zinc present will normally be sufficient to provide zinc complexes.

If the serine protease is sensitive to inhibition by the divalent metal cation, the method further may comprise contacting the compound with a serine protease in a medium having present therein a metal buffering agent capable of reducing the free concentration of the divalent metal cation to the extent that the serine protease is not substantially inhibited by the presence of the divalent metal cation while providing sufficient divalent metal cation by exchange equilibrium to produce the interaction. A typical metal buffer agent will have a $K_d$ for chelation of the relevant divalent metal cation and will be present in suitable amounts such that the free concentration of the divalent metal cation is reduced to the extent that the cation is less available for association with the serine protease but the cation is available for association simultaneously with the protease and the protease inhibitor. Thus, the metal buffering agent will sequester all or most of the dissociated cation and readily transfer the cation to form a binary complex with the inhibitor or a ternary complex with inhibitor and protease (herein defined as exchange equilibrium). For example, a preferred method for determining the serine protease inhibitory activity of a compound wherein zinc is present in the medium and the serine protease is sensitive to inhibition by the zinc, further may comprise contacting the compound with a serine protease in a medium having present therein oxalate as the metal buffering agent.

Methods by which the concentration of the divalent metal cation can be modified and that fall within the intended scope of this invention include, but are not limited to, adding an appropriate amount of the divalent metal cation to the assay medium after the compound is contacted with the protease, mixing the assay reagents together with an appropriate amount of the divalent metal cation such that the desired final concentration of the divalent metal cation in the assay medium is achieved, selecting assay reagents by the levels of the divalent metal cation that are incidentally present so that after combining the reagents the final concentration of the divalent metal cation in the assay medium is achieved, and any other method that is applied for the purpose of adjusting the concentration in the assay medium such that it falls within the limitations of this invention.

Preferred is a method for determining whether the inhibitory activity of a serine protease inhibitor is enhanced by the presence of a divalent metal cation selected from the group consisting of zinc and cobalt, which method comprises:

(a) assaying for the inhibition of a serine protease by the inhibitor, wherein the assay is conducted in a medium that is essentially devoid of dissociated divalent metal cations; and (b) assaying for the inhibition of the serine protease by the compound under essentially equivalent assay conditions to those used in Step (a), with the exception that the assay performed in Step (b) is conducted in a medium that contains an effective concentration of the divalent metal cation; wherein the inhibitory activity of the compound when measured by Step (b) is significantly greater than the inhibitory activity of the compound when measured by Step (a); more preferably wherein the divalent metal cations are removed from the medium used in Step (a) by the presence of a cation sequestering agent and most preferably wherein the divalent metal cation is zinc.

A typical cation sequestering agent will have a $K_d$ for chelation of the relevant divalent metal cation such that the divalent metal cation is not available for association with the compound. For example, cation sequestering agents suitable in the practice of this invention include ethylenediaminetetraacetic acid (EDTA), phenanthroline, and any other common cation sequestering agent which has no effect on the protease activity on its own, preferably EDTA). Standard assay formats for the practice of this invention utilize the serine protease of choice and short peptide substrates whose cleavage can be monitored, typically by simple colorimetric methods. For the purposes of this invention, the inhibitory activity of a compound when measured by Step (b) is considered to be significantly greater than the inhibitory activity of the compound when measured by Step (a) if the difference in the activity is such that one of ordinary skill in the art would consider it substantive in view of typical biological and experimental variablity. Typically, a significantly greater activity will mean at least a ten, preferably at least a one hundred and more preferably at least a one thousand, fold increase in inhibitory activity.

Preferred is a method for inhibiting a serine protease with a divalent metal cation selected from the group consisting of zinc and cobalt in a medium comprising the serine protease and the inhibitor, in which the inhibitor comprises two heteroatoms in spatial relationship one to the other so as to chelate zinc, which method comprises having sufficient quantity of the divalent metal cation in the medium or adding a sufficient amount of the divalent metal cation to the medium to have any or all of the inhibitor which is bound to the serine protease as a divalent metal cation ternary complex, or providing the inhibitor as a divalent metal cation binary complex, such that the divalent metal cation is bound between the inhibitor and the active site of the serine protease as a divalent metal cation ternary complex; more preferably wherein the two heteroatoms are annular members of a ring, particularly wherein at least one of the heteroatoms is an annular member of an benzimidazole ring, or wherein the inhibitor is provided as a zinc binary complex. Suitable zinc binary complexes of compounds can be prepared by combining the compound with a zinc concentration of at least 0.01 $\mu$M to 100 mM, typically 0.1 $\mu$M to 50 mM and preferably about 5 $\mu$M to 50 $\mu$M.

Preferred methods of this invention for inhibiting a serine protease with a serine protease inhibitor are those in which the amount of zinc included in the assay medium is at least equal to the concentration of the serine protease inhibitor. Generally, the amount of zinc included in a preparation or medium containing the inhibitor will be at least 0.1 $\mu$M, typically to least 1 $\mu$M, more preferably 10 $\mu$M, and more preferably at least 100 $\mu$M. Typically, the zinc concentration employed will provide that at least about 80%, preferably at least about 90%, and more preferably substantially all of the inhibitor will be chelated with zinc. In physiological systems, the amount of zinc present will normally be sufficient to provide zinc complexes.

Preferred is a method for inhibiting a serine protease with a serine protease inhibitor comprising a bis(benzimidazole) in a medium comprising the serine protease and the inhibitor, wherein the inhibitor comprises nitrogen atoms of the bis(benzimidazole) in spatial relationship to chelate zinc, the improvement which comprises: adding sufficient zinc to the medium to have all of the inhibitor which is bound to the serine protease as a zinc complex or providing the inhibitor as a zinc binary complex; more preferably wherein the bis(benzimidazole) is substituted with an amidino group.

Preferred is a divalent metal cation binary complex of a compound of Formula II:

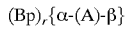

$$(B_p)_r\{\alpha\text{-}(A)\text{-}\beta\} \qquad \text{II}$$

in which:
$B_P$ is a binding moiety for binding to one or more P sites of a serine protease;
r is 0 or 1, with the proviso that at least one $B_P$ binding moiety is present;
A is a bond or a linking group selected from alkylene, heteroalkylene, cycloalkylene, arylene and heteroarylene, which linking group separates $\alpha$ and $\beta$ by one to two atoms and is optionally substituted with 1 to 2 radicals selected from oxo, hydroxy, ($C_{1-2}$)alkyloxy, halo, mercapto, ($C_{1-2}$)alkylthio, amino, ($C_{1-2}$)alkylamino and di($C_{1-2}$)alkylamino, wherein heteroatoms are bonded only to carbon or hydrogen; and
$\alpha$ and $\beta$ each are independently a group comprised by two to thirty six carbon atoms, typically two to eighteen and more preferably two to twelve, and one to eight heteroatoms, wherein at least one heteroatom contained within each of $\alpha$ and $\beta$ is within three, typically two and more preferably one, atoms of A and within six, typically four, atoms of the other heteroatom. Optionally $\alpha$ and $\beta$ are linked via a linking group selected from alkylene and heteroalkylene, which group is optionally substituted with 1 to 2 radicals selected from oxo, hydroxy, ($C_{1-2}$)alkyloxy, halo, mercapto, ($C_{1-2}$)alkylthio, amino, ($C_{1-2}$)alkylamino and di($C_{1-2}$)alkylamino, wherein heteroatoms are bonded only to carbon or hydrogen, in such a manner so that the two related heteroatoms are sterically positioned in spatial relationship one to the other so as to facilitate a bidentate chelation of the divalent metal cation.

More preferred is a compound of Formula II in which $\alpha$ and $\beta$ are independently a group comprised by a heterocycloalkyl or heteroaryl moiety bonded directly or indirectly to A, or a group comprised by an alkyl, cycloalkyl, aryl, heterocycloalkyl or heteroaryl moiety substituted with a heteroatom containing moiety, wherein at least one annular or non-annular heteroatom contained within each of $\alpha$ and $\beta$ is within three, typically two and more preferably one, atoms of A and within six, typically four, atoms of the other heteroatom.

Also preferred is a divalent metal cation binary complex of a compound of Formula III:

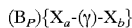

$$(B_P)\{X_a\text{-}(\gamma)\text{-}X_b\} \qquad \text{III}$$

in which:
$B_P$ is a binding moiety for binding to one or more P sites of a serine protease; and
$\gamma$ is an aromatic or non-aromatic, saturated or unsaturated, fused polycyclic hydrocarbon comprised by six to eighteen carbon atoms; and
$X_a$ and $X_b$ are independently an annular heteroatom contained within $\gamma$ or a heteroatom containing moiety bonded directly to $\gamma$, wherein $X_a$ and $X_b$ are within six, typically four, atoms of each other.

Representative divalent metal cations include cobalt and zinc. Zinc is one of the more common divalent metal cations present in physiological tissues and fluids, typically present at 10–100 $\mu$M concentrations. Accordingly, preferred embodiments of this invention include zinc as the divalent metal cation.

Representative first $B_P$ binding moieties comprise a basic group bonded to the α or β group through a carbon atom, which basic group generally is comprised of carbon, hydrogen, nitrogen and/or oxygen, typically of not more than 10, preferably not more than 6, atoms other than hydrogen (e.g., guanidino, amidino, aminomethyl, amino higher alkyl, α-aminocarboxymethyl, α-aminocarboxamidemethyl, and the like). A representative second $B_P$ binding moiety generally is comprised of carbon, hydrogen, nitrogen and/or oxygen, typically of not more than 20 atoms other than hydrogen (e.g., alkyl, non-oxo carbonyl, amino, aminoalkyl, amidino, or the like). Further, a $B_P$ binding moiety may be an amino acid radical, particularly argininyl or lysinyl, may be an oligopeptide radical which is the specific target site for the target serine protease (e.g., amidino, amino, guanidino, or other basic moiety for trypsin-like serine proteases and carboxylates or lipophilic groups for chymotrypsin-like proteases).

Representative A linking groups include methylene, methene, carbonyl, amino, oxy, thio, isopropylidene, 1,2-cyclohexylene, 1,2-phenylene, and the like.

The α and/or β groups may have one or more heteroatom containing substituents other than the heteroatoms involved in chelating. The substituents will usually be not more than 6 carbon atoms, more usually not more than 3 carbon atoms and may include amino of from 0 to 6 carbon atoms, non-oxo-carbonyl of from 1 to 6 carbon atoms, particularly salts, esters and amides, and the sulfur and nitrogen analogs thereof, hydroxy or alkyloxy of from 0 to 6 carbon atoms, or aryloxy, halo, cyano, nitro, oxo, etc.

Representative α and/or β heteroaryl groups preferably have at least one $sp^2$ nitrogen atom and include five membered rings, such as pyrazole, imidazole, triazole, oxazole, thiazole, isoxazole, etc. and benzo-fused derivatives thereof, such as benzimidazole, etc., six membered rings such as pyran, pyridine, pyridazine, pyrimidine, pyrazine, dioxane, etc. and benzo-fused derivatives thereof, such as quinoline, isoquinoline, cinnoline, etc., and non-fused rings, such as 2,2'-bis-imidazole, 2,2'-bis(pyridine), etc. The heteroaryl groups are optionally substituted with 1 to 3 radicals selected from halo, alkyloxy, amino, cyano, non-oxo-carbonyl, alkyl, or any other common substituent, preferably electron-donating, which do not sterically preclude binding or completion steps necessary for the inhibitor to function. Additional representative α and β groups include methoxymethyl, aminomethyl, methylaminomethyl, guanidinomethyl, amidinomethyl, anilinomethyl, 2,3-diaminopropyl, 2-amino-3-hydroxypropyl, 2-amino-2-trifluoromethylethyl, 2-hydroxyethyl, substituted aromatics like 2-mercaptophenyl, 2-hydroxyphenyl, 2-aminophenyl, 2-carboxyphenyl and substituted analogs thereof, methylacetoxy, glycinamidomethyl, cyclohexylaminomethyl, and the like.

Representative γ groups include 1,8-naphthalenylene, 8-cinnolinyl, 5,6-phenanthrenylene, 1,8-dihydroxynaphthalenylene, and the like, wherein the atom (s) with free valence are bonded to heteroatom containing moiety.

In general, the compounds useful in the practice of this invention will comprise not more than sixty, typically not more than thirty six, carbon atoms and not more than twenty, typically not more than sixteen, preferably not more than twelve and more preferably not more than eight, heteroatoms. For example, representative serine protease inhibitors useful in the practice of this invention include 2,2'-bis (benzimidazoles) having one $B_P$ binding moiety at its 5-position and optionally having a second benzimidazolyl moiety in its 4'-or 5'-position.

In particular, compounds useful in the practice of this invention include, but are not limited to, bis(5-amidinobenzimidazol-2-yl)methane (Compound 1); bis(5-amidinobenzimidazole)-methanone (Compound 2); 2-(5-aminomethylbenzimidazol-2-ylmethyl)benzimidazole; 2-(5-amino-methylbenzimidazol-2-ylmethyl)-5-methylbenzimidazole (Compound 7); 2-(5-amidino-benzimidazol-2-ylmethyl)benzimidazole (Compound 4); 2-benzimidazol-2-ylethylbenzimidazole; 2-(5-guanidinobenzimidazol-2-ylmethyl)benzimidazole; 2-(5-carboxybenzimidazol-2-ylmethyl)-benzimidazole (Compound 8); 2-(imidazol-2-ylmethyl)-5-amidinobenzimidazole (Compound 6); 5-amidino-2-imidazol-4-ylmethylbenzimidazole; 5-amidino-2-pyrid-2-ylbenzimidazole (Compound 10); 5-amidino-2-pyrid-2-ylmethylbenzimidazole; 1-(5-amidinobenzimidazol-2-yl)-isoquinoline; 2-(5-amidinobenzimidazol-2-yl)quinoline; 3-(5-amnidinobenzimidazol-2-yl)-isoquinoline; 8-(5-amidinobenzimidazol-2-yl)quinoline; 5-amidino-2-(2-hydroxyphenyl)-benzimidazole; 5-amidino-2-(2-mercaptophenyl)benzimidazole; and 5-amidino-2-(2-aminophenyl)-benzimidazole.

The compounds useful in the practice of this invention can be prepared in accordance with known synthetic procedures. See, for example, Tidwell, et al., J. Med. Chem. (1978) 21:613–623; and general methods for the synthesis of substituted and/or fused heterocyclic systems and their isomers, as described in "Comprehensive Heterocyclic Chemistry", Pergamon Press:Oxford, 1988. The inhibitors may be prepared as crude mixtures comprising at least about 50 weight %, typically at least about 90, preferably at least 99, weight % of the composition.

Representative proteases useful in the practice of this invention include, but are not limited to, activated protein C, chymase, chymotrypsin, cytomegalovirus protease, elastase, elastase, factor VIIa, factor IXa, factor Xa, plasm kallikrein, tissue kallikrein, β-lactamases, plasmin, thrombin, trypsin, tryptase and urokinase.

Pharmacology and Utility

The serine protease inhibitors useful in and identified by the practice of this invention, in association with,a divalent metal cation or as a pre-associated binary complex with a divalent metal cation, form a divalent metal cation ternary complex with the active site residues of the serine protease and thereby inhibits its activity. The serine protease inhibitors useful in and identified by the practice of this invention comprise (a) a chemical functional group which occupies the P1 site on the target serine protease and (b) a structurally adjacent bidentate chelator which captures the divalent cation into a tetrahedral complex involving side chains of His57 and Ser195 of the catalytic site of the enzyme. The combination of P1 binding and bidentate chelation properties in a single composition provides a synergistic effect for serine protease inhibition at physiological levels of divalent cations like zinc. For example, benzamidine (Compound 3) and benzylamine (Compound 5), which each have a typical P1 recognition element, are weak inhibitors of the serine protease trypsin. Similarly, 2-pyrid-2-ylbenzimidazole (Compound 9), which comprises a typical zinc sequestering element, produces no inhibition of trypsin. However, 5-amidino-2-pyrid-2-yl-benzimidazole (Compound 10), which comprises the structural combination of the typical P1 binding and zinc sequestering elements, is a potent inhibitor of trypsin. Thus, the serine protease inhibitors useful in and identified by the practice of this invention meet the above-described structural requirements if the value of the $K_i$ (Zinc removed) $>>K_i$ (Zinc added), indicating inhibition is potentiated in the presence of zinc. Accordingly, the methods and compositions of this invention are useful for in vitro and in vivo inhibition of serine proteases and for the screening for and the identification of serine protease inhibitors and for protecting peptides and proteins from proteolytic degradation.

X-ray crystallography of the inhibitor-zinc-serine protease complexes have and can be obtained using contemporary biophysical methodologies and commercial instrumentation. Such crystallographic data have and can be used to conclusively determine if a serine protease inhibitor has the structural requirements necessary for zinc potentiation of serine protease inhibition. An example of such an X-ray crystallographic determination is presented below.

Serine protease enzymes of interest include, but are not limited to, trypsin-like enzymes, such as trypsin, plasm kallikrein, tissue kallikrein, plasmin, thrombin and tryptase; chymotrypsin-like enzymes, including chymotrypsin, cathepsin G. and chymase; elastase-like enzymes, including neutrophil elastase and elastase; and carboxypeptidase-like enzymes. These enzymes play a role in apoptosis, blood pressure regulation, cancer, cardiovascular function, blood clotting, lysis, chemotaxis, development, digestion, fertilization, hormone processing, immune response, complement, infection: bacterial, viral and parasitic inflammation, mast cells, and other cells, neurologic, pain and protein secretion. Serine protease targets in medicine include for cardiovascular treatments: thrombin, factor Xa, factor VIIa, and chymase; for infectious diseases involving parasites, viruses and bacteria: cytomegalovirus protease and β-lactamases, serine proteases specific for the pathogen; for bleeding, urokinase, activated protein C and tPA; for inflammation, tryptase, chymase, neutrophil elastase, plasm kallikrein and tissue kallikrein; and for neurobiology, serine proteases associated with Alzheimer's disease, to name only a few of the available targets.

The methods and compositions of this invention may be used in affinity columns to isolate serine proteases. Furthermore, because the serine protease inhibitors useful in the practice of this invention can vary as to their specificity toward serine proteases, the methods and compositions of this invention can be used to selectively isolate and purify serine proteases. In this regard, conventional techniques may be employed for linking the various compounds to supports, beads, macromolecules, and the like. Linking groups may include carboxyl groups, amino groups, thio groups, activated olefins, or the like. The linking group may be bonded to the inhibition moiety or the binding moiety. Surfaces of columns or capillaries may be employed as the affinity column or the column may be packed with a variety of beads, such as Sephadex, sepharose, latex beads, or the like. The particular manner in which the column is prepared is not critical to the practice to this invention. In addition, the columns may be used in assays for detecting the various serine proteases, by providing a binding profile which can be developed for the serine protease of interest, and determining relative $K_i$ values for libraries of inhibitors that utilize metal complexation as a mechanism of inhibition.

The serine protease inhibitors useful in and identified by the practice of this invention are themselves useful for the treatment of various diseases. For example, serine protease inhibitors can be used for the treatment of clinical arthritis, synovitis and associated pathologies (e.g. see U.S. Pat. No. 4,940,723). The serine proteases useful in and identified by the practice of this invention also permit investigation of the physiological processes associated with a wide variety of biological events involving serine proteases. The advantage of being able to modulate serine protease activity by removing or adding zinc allows for the investigation on the effect of such activity in physiological processes.

Further, because the divalent metal cation-serine protease inhibitor complexes of this invention are able to form the inhibitor-cation-serine protease ternary complex without the necessity of having the concentration of zinc in the assay medium modified, the pre-associated cation-inhibitor complexes are useful in the practice the methods of this invention for identifying the inhibitory activity of the inhibitors. Similarly, the divalent metal cation-serine protease inhibitor complexes of this invention are useful in treating disease wherein the inhibitor is delivered to the target tissue locally (e.g., by topical application to the skin or eyes, by aerosol delivery to the lungs, etc.).

Administration and Pharmaceutical Compositions

In general, the divalent metal cation-serine protease inhibitor complexes of this invention and the serine protease inhibitors useful in and identified by the practice of this invention will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a serine protease inhibitor or complexes thereof for the treatment of asthma may range from 0.1 micrograms per kilogram body weight ($\mu$g/kg) per day to 1 milligram per kilogram body weight (mg/kg) per day, typically 1 $\mu$g/kg/day to 0.1 mg/kg/day. Therefore, a therapeutically effective amount for a 80 kg asthmatic human patient may range from 10 $\mu$g/day to 10 mg/day, typically 0.1 mg/day to 10 mg/day. In general, one of ordinary skill in the art, acting in reliance upon personal knowledge and the disclosure of this application, will be able to ascertain the therapeutically effective amounts of the serine protease inhibitors for treating a given disease.

Serine protease inhibitors can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a serine protease inhibitor in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the active ingredient in aerosol form. Inert gases suitable for this purpose are nitrogen, carbon dioxide, nitrous oxide, etc.

Other suitable pharmaceutical carriers and their formulations are described in A. R. Alfonso *Remington's Pharmaceutical Sciences* 1985, 17th ed. Easton, Pa.: Mack Publishing Company.

The amount of a serine protease inhibitor or metal cation complex thereof in the composition may vary widely depending upon the type of formulation, size of a unit dosage, kind of excipients and other factors known to those of skill in the art of pharmaceutical sciences. In general, a composition of a serine protease or metal cation complex thereof will comprise from 0.01%w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required.

EXAMPLES

Example 1

In Vitro Enzyme Inhibitor Assay

The following represents an assay for determining the serine protease inhibitory activity of a compound.
Step (a)—Zinc Removed Mixtures of human trypsin (3.4 nM) and test compound (varying concentrations) in assay medium (comprising: DMSO, 10%; polyoxyethylenesorbitan monolaurate (Tween-20), 0.05%; and EDTA; 1 mM; in buffered saline adjusted to pH 8.0) were incubated for 1 hour at room temperature and then substrate, N-tosyl-gly-pro-lys-pNA (Sigma #T6140, 0.5 mM in water), was added such that the final concentration of the assay mixture was 0.125 mM. Hydrolysis of the substrate was followed spectrophotometrically at (405 nm) for 5 minutes. Apparent inhibition constants ($K_i$) were calculated from the enzyme progress curves using standard mathematical models.
Step (b)—Zinc Modified The assay protocol for determination of inhibition in the presence of zinc is conducted under essentially equivalent assay conditions to that used for Part (a), with the exception that the assay medium does not contain EDTA and is modified to 150 $\mu$M zinc chloride in the form of a stock solution of 100 mM.
Step (c)—Zinc Ambient The assay protocol for determination of inhibition at ambient levels of zinc is conducted under essentially equivalent assay conditions to that used in Part (a), with the exception that the assay medium does not contain EDTA.

Proceeding as in Example 1, compounds of Formula I were tested for their inhibitory activity toward activated protein C, chymase, chymotrypsin, factor Xa, factor VIIa, plasm kallikrein, tissue kallikrein, β-lactamase, plasmin, thrombin, trypsin, tryptase and urokinase. Compounds of Formula I were identified for each protease wherein the inhibitory activity of the compound when measured by Step (b) was at least $10^1$, typically $10^2$ to $10^3$, times greater than the inhibitory activity of the compound when measured by Step (a).

Proceeding as in Example 1, Part (b), but varying the zinc concentration in the medium from $10^{-9}$M to $10^{-4}$M, assays were performed which demonstrated that the minimum zinc concentration found to maximally enhance the inhibitory activity of a compound was between 0.1 and 1 $\mu$M.

Example 2

In Vitro Enzyme Inhibitor Assay

The following represents an assay for determining the serine protease inhibitory activity of a compound in the presence of a metal buffering agent.
Part (a)—Zinc Removed Mixtures of cytomegalovirus (CMV) protease (50 nM) and test compound (varying concentrations) in assay buffer (comprising: HEPES, 50 mM; NaCl, 150 mM, PEG 3350, 0.01% Sucrose, 30%, oxalate, 4.5 mM; adjusted to pH 7.5) were incubated for 15 minutes at room temperature and then substrate dabsyl-arg-gly-val-val-asn-ala-ser-ser-arg-leu-ala-lys-lys-dansyl (SEQ ID NO: 1) (4 mM in water), was added such that the final concentration of the assay mixture was 10 $\mu$M. Hydrolysis of the substrate was followed fluorometrically (ex 355 nm, em 510 nm) for approximately 15 minutes. Apparent inhibition constants (Ki) were calculated from the enzyme progress curves using standard mathematical models.
Part (b)—Zinc Modified The assay protocol for determination of inhibition in the presence of zinc is conducted under essentially equivalent assay conditions to that used for Part (a), with the exception that the assay is modified to 10 $\mu$M zinc.

Proceeding as in Example 2, compounds of Formula I were tested for their inhibitory activity toward CMV protease. Compounds of Formula I were identified wherein the inhibitory activity toward CMV protease when measured by Step (b) was 30 to $10^2$ times greater than the inhibitory activity of the compound when measured by Step (a).

Proceeding as in Example 2, Part (b), but substituting trypsin for CMV protease and varying the zinc concentration in the medium from $1\times10^{-9}$M to $1\times10^{-4}$M, assays were performed which demonstrated that the minimum zinc concentration needed to maximally enhance the inhibitory activity of a serine protease inhibitor was between 0.1 and 1 $\mu$M.

TABLE 1

The following table represents representative results from assays conducted as described in Examples 1 and 2.

| | | Inhibition, ($K_i$, $\mu$M ± S.D.) | | |
|---|---|---|---|---|
| | protease | $[Zn]_{ambient}$ | $[Zn]_{removed}$ | $[Zn]_{modified}$ |
| Compound 1 | trypsin | 0.1, 0.01 | 88 | 0.4, 0.003 |
| | plasmin | 1.3 | 28.8, >1000 | 0.004 ± 0.003 |
| | thrombin | 1.9 ± 1.6 | | 0.06 ± 0.09 |
| | factor Xa | 0.04, 0.02 | | <0.001, <0.001 |
| | chymotrypsin | | 709, >1000 | 120, 69.4 |
| | activated protein C | | 55.1, 22.3 | 0.02, 0.006 |
| | TEM β-lactamase | | >1000 | 25 |

TABLE 1-continued

The following table represents representative results from assays conducted as described in Examples 1 and 2.

| | | Inhibition, ($K_i$, $\mu$M ± S.D.) | | |
| --- | --- | --- | --- | --- |
| | protease | $[Zn]_{ambient}$ | $[Zn]_{removed}$ | $[Zn]_{modified}$ |
| Compound 2 | trypsin | 50 | 35 | 0.5 |
| | factor Xa | 0.05 | | 0.3 |
| | thrombin | >1000 | | 0.08 |
| Compound 3 | trypsin | 325 | 266 | 273 |
| Compound 4 | trypsin | 0.02 | 151 ± 32 | 0.01 ± 0.01 |
| | plasmin | | >1000 | 0.009 |
| | thrombin | 0.9 ± 0.7 | | 0.01 ± 0.005 |
| | factor Xa | 0.04 ± 0.01 | | 0.0004 ± 0.0005 |
| | activated protein C | | 117, >1000 | 0.009, 0.301 |
| | urokinase | | >1000, >1000 | 1.05, 1.05 |
| | tissue kallikrein | | 267 | 1.4, 20.8 |
| | plasma kallikrein | | 1.3 | 0.002 |
| | tryptase | | 13.5 | 0.07 |
| | factor VIIa | 10 | | 0.07 |
| Compound 5 | trypsin | >1000 | 344 | 354 |
| Compound 6 | trypsin | >1000 | >1000 | 32.8 |
| Compound 7 | trypsin | 808 | >1000 | 1.5 |
| | tryptase | 64.6 | 85.9 | 0.4 |
| Compound 8 | trypsin | 1.3 | >1000 | 1.9 |
| | tryptase | 17 | 35 | 4.3 |
| Compound 9 | trypsin | >1000 | >1000 | >1000 |
| Compound 10 | trypsin | 748 | 184 ± 104 | 15 ± 6.3 |
| | plasmin | | >1000 | 4.7 |
| | thrombin | 45.5, 81.5 | | 0.5, 0.7 |
| | factor Xa | 0.3, 0.7 | | 0.03, 0.03 |
| | chymotrypsin | | 702 | 403 |
| | activated protein C | | >1000 | 3.8 |
| | tryptase | 45 | | 1.6 |
| | factor VIIa | 106 | | 1.4 |
| Compound 11 | trypsin | | 426 | 1.3 |
| | plasmin | | >1000 | 0.03 |
| | thrombin | | 312 | 0.2 |
| | factor Xa | 0.6 | | 0.002 |
| | chymotypsin | | >1000 | 90 |
| | activated protein C | | 511 | 1.9 |
| Compound 12 | CMV | | >1000 | 12 |
| Compound 13 | plasma kallikrein | | 95 | 0.004 |
| Compound 14 | chymase | | 350 | 0.01 |
| Compound 15 | urokinase | | >1000 | 0.02 |
| Compound 16 | TEM β-lactamase | | >1000 | 0.64 |
| | AmpC β-lactamase | | >1000 | 0.22 |

Example 3

X-Ray Crystallography of Serine Protease-Zinc-Protease Complex

Crystals of Compound3-trypsin were grown using MgSO$_4$ as the precipitant in 100 mM Tris, pH 8.2 by the batch 5 method of M. Krieger, L. M. Kay and R. Stroud, J. Mol. Biol. 83:209–230(1974). Compound 1-trypsin could not be crystallized de novo, nor with seeding with Compound 3-trypsin crystals. Initial attempts to soak Compound 1 into these crystals at pH 8.2 were unsuccessful because of limited solubility and stability of Compound 1 at this pH in MgSO$_4$-containing synthetic mother liquor. Moreover, in Tris buffer alone at pH 8.2 Compound 1 turns yellow within an hour, and after many hours begins to precipitate. In MES buffer at pH 5.9 this transformation does not occur after several weeks. The solubility of Compound 1 freshly dissolved in synthetic mother liquor containing 415 mg/ml MgSO$_4$, 100 mM Tris, pH 8.2 or 415 mg/ml MgSO$_4$, 100 mM MES, pH 5.9 was determined to be ~100 mM.

Crystals of Compound 1-trypsin (pH 5.9) were first prepared successfully by soaking Compound 3-trypsin crystals in freshly dissolved Compound 1 in synthetic mother liquor at saturation at pH 5.9. The soaks were replaced with fresh ones 4 times, about once a day. Crystals of Compound 1-trypsin (pH 8.2) were successfully prepared by soaking Compound 3-trypsin crystals in freshly dissolved Compound 1 in synthetic mother liquor at saturation at pH 8.2 containing 0.1 mM ZnSO$_4$. The soaks were replaced with fresh ones 5 times, about once a day. Significant amounts of yellow precipitate formed in the soaking solutions after a day.

Individual $I_{hkl}$ data were collected for Compound 3-trypsin (pH 8.2), Compound 1-trypsin (pH 5.9) and Zn$^{+2}$-Compound 1-trypsin (pH 8.2) on a Siemens Multiwire Area Detector or on an image plate detector (R-axis-II (Rigaku Corporation)). Data were extracted using the XDS programs of Kabsch, or the software provided by the Macromolecular Structure Corporation, (The Woodlands, Tex.), and an indexing program. Data collection and refinement statistics are listed in Table 2.

For the refinement of Compound 3-trypsin, the highly refined MIP-trypsin structure served as a template. Water molecules outside the active site region in the MIP X-ray and neutron structures were included in the initial phasing model. The structure was refined using alternating cycles of ($|Fo|-|Fc|$), $\alpha_c$ and ($2|Fo|-|Fc|$), $\alpha_c$ difference maps (J. L. Chambers & R. Stroud, Acta Cryst. B35: 1861–1875 (1979), and automated least squares refinement with XPLOR (Brünger) Difference Fourier maps were computed between Compound 3-trypsin (pH 8.2) and Compound 1-trypsin (pH 5.9) or $Zn^{+2}$-Coumpound 1-trypsin (pH 8.2) to yield initial structures which were then likewise refined.

The ($2|Fo|-|Fc|$), $\alpha_c$ difference map for Compound 1-trypsin at pH 5.9 clearly shows one amidinobenzimidazole group of Compound 1 occupying the P1 pocket. The Compound 1 molecule pivots to an altered position in the structure of trypsin-Compound 1-$Zn^{+2}$ at pH 8.2, to allow the benzimidazoles of Compound 1 to form part of the $Zn^{+2}$ binding site. The pivoting causes an insignificant change in the position of the amidine group in the P1 pocket, but a large shift (~5 Å) in the position of the other amidine group. An NH group of one terminal amidine nitrogen interacts with main chain carbonyl 41 through bridging hydrogen bonds, while another NH group of the other terminal amidine nitrogen forms a direct hydrogen bond with the main chain carbonyl 244 of a symmetry related molecule.

TABLE 2

The following table represents the results of the Crystallography of Trypsin-Compound 3, Trypsin-Compound 1-$SO_4^{-2}$, pH 5.9, and Trypsin-Compound 1-$Zn^{+2}$, pH 8.2.

|  | Trypsin-Cpd 3 | | Trypsin- Cpd 1-$SO_4^{-2}$ | Trypsin- Cpd 1-$Zn^{+2}$ |
|---|---|---|---|---|
|  | (1BNZ) | (2BNZ) |  |  |
| Parameters |  |  |  |  |
| # Atoms (including disorder) | 4114[a] | 4095[a] | 1926 | 1955 |
| # Waters (including disorder) | 225 | 229 | 211 | 214 |
| # discretely disordered groups[b] | 23 | 18 | 20 | 21 |
| # Discretely disordered waters | 2 | 5 | 4 | 7 |
| # Side chains with refined occs[c] | 12 | 13 | 16 | 13 |
| # Waters with refined occs | 90 | 91 | 0 | 0 |
| Diffraction Statistics |  |  |  |  |
| Resolution[d] (Å) | 8.00–1.50 | 7.00–1.70 | 8.00–1.87 | 8.00–2.04 |
| # Observations |  | 63142 |  |  |
| # Reflections[d] | 24173 | 17697 | 11673 | 8337 |
| F/σ cutoff | 2.4 | 0 | 1.0 | 1.0 |
| $R$merge[e] (%) | 16.1 | 15.4 | 7.9 | 8.5 |
| $R$cryst[f] (%) | 16.1 | 15.4 | 13.2 | 15.5 |
| Completeness[e] | 69.2 | 69.4 | 63.7 | 57.0 |
| Rms deviations[g] |  |  |  |  |
| Bond lengths (Å) | 0.016 | 0.016 | 0.014 | 0.017 |
| Bond angles (°) | 3.7 | 3.7 | 2.9 | 3.8 |
| Torsion angles (°) | 26.7 | 26.3 | 26.1 | 26.4 |

[a]restrained, isotropic temperature factors were refined for all structures. Hydrogen atoms were included in the refinement of the Compound 3-trypsin structures.
[b]not including waters.
[c]Density for all side chain atoms or for terminal atoms in there groups was weak absent and temperature factors were high. Discretely disordered groups are not included in this category. Occupancies for poorly defined atoms were refined.
[d]refers to refinement limits.
[e]R merge = $\Sigma h \Sigma I |I(h)I - <I(h)>|/\Sigma_h \Sigma_I I(h)_I$, where $I(h)_I$ is the ith observation of the intensity of reflection h.
[f]Rcryst = $\Sigma(F_o - F_c)/\Sigma F_o$.
[g]Root mean square deviations from ideal bond lengths and bond angles.

pound 3 portion of it closely overlays that for Compound 3 in the Compound 3-trypsin structure. At pH 8.2, the ($|Fo|-|Fc|$), $\alpha_c$ and ($2|Fo|-|Fc|$), $\alpha_c$ maps for the $Zn^{+2}$-Compound 1-trypsin complex clearly reveal the position and orientation of Compound 1 as well as a strong peak (13 σ in the ($|Fo|-|Fc|$), $\alpha_c$ map) which corresponds to the position of the $Zn^{+2}$ ion coordinating two of the imidazole nitrogens of Compound 1, the imidazole of His57 and the Oγ atom of Ser195. Thus the nanomolar binding constant of Compound 1 is achieved with the synergy of $Zn^{+2}$ at concentrations of this metal at lower than 100 nM. Bond distances involving the $Zn^{+2}$ ion, are similar to those observed in other $Zn^{+2}$-containing proteins. The average of 5 ligand-$Zn^{+2}$-ligand angles is 114(11)°, but the 6th angle, involving the Compound 1 ligand alone (N3—$Zn^{+2}$—N3') is only 81°. The It is evident from the above results, that by using metal cation complexes, particularly zinc, or metal cation complexes involving, particularly zinc, in combination with compounds comprising a P site binding moiety and a metal cation chelating moiety, which compounds can fit at the active site, extremely active serine protease inhibitors can be produced, By modifying the P site binding moiety, the chealating compounds can be directed to a viriety of different serine proteases with high specificity. In this manner, one may inhibit serine protease activity in vitro and in vivo, in studying physiological processes, in preventing degradation of proteins which are specific substrates of serine proteases, in inhibiting bacteriological action, and in treating a variety of indications, where the pathology is associated with active serine proteases.

We claim:

1. A method for determining whether a compound has serine protease inhibitory activity, the method comprising:
  (a) contacting a serine protease with a serine protease substrate in the presence of a divalent metal cation and measuring a first amount of serine protease activity,
  (b) contacting the compound with the serine protease and the serine protease substrate in the presence of the divalent metal cation and measuring a second amount of serine protease activity, and
  (c) comparing the first amount and second amounts of serine protease activity to determine whether the compound has serine protease inhibitory activity;
  wherein
    (i) the divalent metal cation is capable of potentiating any inhibitory activity of the compound,
    (ii) the serine protease is sensitive to inhibition by the divalent metal cation, and
    (iii) Steps (a) and (b) are conducted in a medium wherein a portion of divalent metal cation is bound by an oxalate present in an amount which reduces the free concentration of the divalent metal cation to the extent that the serine protease is not substantially inhibited by the divalent metal cation while providing sufficient divalent metal cation by equilibrium exchange to have any or all of the compound in a binary complex with the metal cation or in a ternary complex with the divalent metal cation and the protease.

2. The method of claim 1, wherein the divalent metal cation is selected from a group consisting of zinc and cobalt.

3. The method of claim 1 wherein Steps (a) and (b) are conducted in a medium wherein the concentration of the free divalent metal cation in the medium is modified to at least 0.1 $\mu$M.

4. The method of claim 1 wherein Steps (a) and (b) are conducted in a medium wherein the concentration of the free divalent metal cation in the medium is modified to at least 1.0 $\mu$M.

5. The method of claim 1 wherein Steps (a) and (b) are conducted in a medium wherein the concentration of the free divalent metal cation in the medium is modified to at least 10 $\mu$M.

6. The method of claim 1 wherein Steps (a) and (b) are conducted in a medium wherein the concentration of the free divalent metal cation in the medium is modified to at least 100 $\mu$M.

7. The method of claim 1, wherein the serine protease is selected from the group consisting of activated protein C, chymase, chymotrypsin, cytomegalovirus protease, elastase, factor VIIa, factor IXa, factor Xa, plasm kallikrein, tissue kallikrein, $\beta$-lactamase, plasmin, thrombin, trypsin, tryptase and urokinase.

8. A method for determining the potentiating activity of a divalent metal cation on a serine protease inhibitor, which method comprises:

(a) contacting the inhibitor with a serine protease and a serine protease substrate in the presence of a first concentration of a divalent metal cation and measuring a first amount of serine protease inhibition, (b) contacting the inhibitor with the serine protease and the serine protease substrate in the presence of a second concentration of the divalent metal cation and measuring a second amount of serine protease inhibition, and (c) comparing the first amount and second amounts of serine protease inhibition to determine the potentiating activity of the divalent metal cation on the serine protease inhibitor wherein (i) the serine protease is sensitive to inhibition by the divalent metal cation, and (ii) Steps (a) and (b) are conducted in a medium wherein a portion of divalent metal cation is bound by an oxalate present in an amount which reduces the free concentration of the divalent metal cation to the extent that the serine protease is not substantially inhibited by the divalent metal cation while providing sufficient divalent metal cation by equilibrium exchange to have any or all of the compound in a binary complex with the divalent metal cation or in a ternary complex with the divalent metal cation and the protease.

9. The method of claim 8, wherein the serine protease is selected from the group consisting of activated protein C, chymase, chymotrypsin, cytomegalovirus protease, elastase, factor VIIa, factor IXa, factor Xa, plasma kallikrein, tissue kallikrein, β-lactamase, plasmin, thrombin, trypsin, tryptase and urokinase.

* * * * *